United States Patent [19]

Otsuka et al.

[11] 4,278,509
[45] Jul. 14, 1981

[54] METHOD OF ACTIVATING OXYGEN CONCENTRATION CELL

[75] Inventors: Yasuhiro Otsuka; Ryuzo Hori; Shinichi Matsumoto; Kiyoshi Uchida; Toshinobu Furutani, all of Toyota, Japan

[73] Assignee: Toyota Jidosha Kogyo Kabushiki Kaisha, Toyota, Japan

[21] Appl. No.: 101,711

[22] Filed: Dec. 10, 1979

Related U.S. Application Data

[63] Continuation of Ser. No. 933,476, Aug. 14, 1978

[30] Foreign Application Priority Data

Apr. 19, 1978 [JP] Japan .................. 53-46080

[51] Int. Cl.³ .................................. G01N 27/46
[52] U.S. Cl. .......................... 204/1 T; 204/195 S
[58] Field of Search ...................... 204/1 S, 195 S

[56] References Cited

U.S. PATENT DOCUMENTS

| | | | |
|---|---|---|---|
| 3,576,730 | 4/1971 | Spacil | 204/195 S |
| 3,773,641 | 11/1973 | Fitterer | 204/195 S |
| 3,871,981 | 3/1975 | Flais et al. | 204/195 S |
| 4,096,048 | 6/1978 | Matsumoto et al. | 204/195 S |

Primary Examiner—T. Tung
Attorney, Agent, or Firm—Brisebois & Kruger

[57] ABSTRACT

In an oxygen concentration cell having metal electrodes formed on both inner and outer wall surfaces of its solid electrolyte vessel and a solid pole as a reference oxygen partial pressure source made of a metal alone or a mixture of a metal and an oxide of the metal filled in said vessel, a method of activating said oxygen concentration cell by heat-treating the cell so as to diffuse the metal of said reference oxygen partial pressure source into said metal electrode on the inner wall or into said solid electrolyte through the metal on the inner wall surface and the oxygen concentration cell produced by this method.

5 Claims, 7 Drawing Figures

METHOD OF ACTIVATING OXYGEN CONCENTRATION CELL

This is a continuation of application Ser. No. 933,476 filed Aug. 14, 1978.

BACKGROUND OF THE INVENTION

This invention relates to a method of activating an oxygen concentration cell and the oxygen concentration cell produced.

Generally, an oxygen concentration cell includes a vessel made of a solid electrolyte which is a specific ceramic material having oxygen-ion conductivity, and it detects the oxygen concentration of a gas portion to be measured by measuring electromotive force generated by the difference of an oxygen partial pressure between the gas portion to be measured and a reference gas portion. The oxygen concentration cell may be divided roughly into the following two groups; as the reference oxygen partial pressure source, one using the oxygen in the air and the other using an equilibrium oxygen partial pressure between a metal and an oxide of the metal.

The conventional oxygen concentration cell of the latter type using a metal and its oxide for a solid pole as the reference oxygen partial pressure source has the drawbacks of inferior low temperature performance and poor load characteristics because the internal impedance of the cell is high at the initial stage. When the oxygen concentration cell is connected to a system, the cell is under the same condition as if it were wired to a load resistor when viewed from the side of the cell. For this reason, a voltage detected from the oxygen concentration cell drops. Especially when the oxygen concentration cell is used in the low temperature range, a drastic voltage drop occurs, thereby prohibiting the action of the system as whole. In other words, when a load is wired to the oxygen concentration cell, the terminal voltage of the cell is directly associated with its internal impedance.

SUMMARY OF THE INVENTION

It is an object of the present invention to provide a method of activating an oxygen concentration cell by diffusing a metal used as a reference oxygen partial pressure source into a metal electrode or a solid electrolyte of the cell.

It is another object of the present invention to provide an oxygen concentration cell having good load characteristics and excellent low temperature performance.

It is still another object of the present invention to provide an oxygen concentration cell which can be used as an oxygen sensor, an oxygen-meter or the like.

DETAILED DESCRIPTION OF PREFERRED EMBODIMENT

This invention relates to a method of activating an oxygen concentration cell and to the oxygen concentration cell obtained by said method.

The following explanation will be given with primary reference to an oxygen sensor by way of example because the oxygen concentration cell is principally used as the oxygen sensor. It is to be understood, however, that the present invention is not specifically so restricted.

Figure 1:
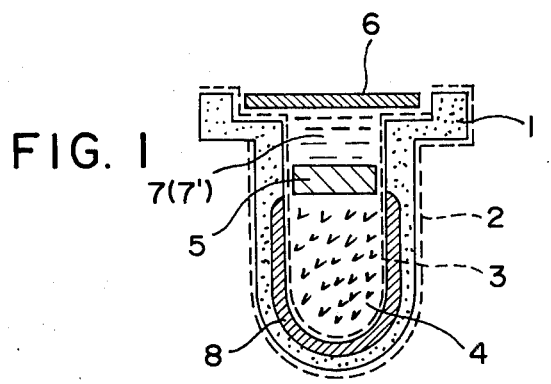
FIG. 1 is a sectional view of an oxygen sensor activated by the method of this invention.

An embodiment of the method of the invention will be described by referring to the accompanying drawings, wherein FIG. 1 is a sectional view of the oxygen sensor in accordance with the present invention. On both inner and outer wall surfaces of a solid electrolyte vessel 1 having a substantially U-shaped sectional shape, there are formed respectively an outer surface metal electrode 2 and an inner surface metal electrode 3, each having a thickness of about 3 microns, by the thermal decomposition method of a platinum salt. Next, a powder is prepared by adding, for example, an alumina powder as a sintering-inhibiting agent to various metals alone or to a mixture of the metal and its oxide, and the powder so prepared is filled into the solid electrolyte vessel 1 to thereby form a solid pole 4. Further onto the solid pole 4 are fitted a ceramic plate 5 consisting of a ZrO$_2$ sheet, a glass sheet 7 and a ceramic plate 6 in the order named. The element thus constructed is heated, for example, to 1,000° C. for 10 minutes in an electric furnace to fuse the glass sheet 7 into a glass layer 7' and thus to make the sealing treatment.

When the whole oxygen sensor obtained by the above-mentioned method is further subjected to the heat-treatment, the metal of the reference oxygen partial pressure source packed into the solid electrolyte vessel 1, that is, the metal of the solid pole 4, is diffused into the inner surface metal electrode 3 or into the solid electrolyte vessel 1 passed through the inner surface metal electrode 3 to form a diffusion layer 8. Duffusion of the metal of the solid electrode is also effective into the inner surface metal electrode. However, it is preferred to diffuse the metal in 0–85% of the wall thickness of the solid electrolyte vessel through the inner surface metal electrode, and above all, it is effective to diffuse the metal from 0 to 60% of the wall thickness of the vessel.

The oxygen ions that have passed through the solid electrolyte 1 are converted to the oxygen atoms or moleculars on the electrode 3 in accordance with the following formula:

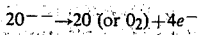

$$2O^{--} \rightarrow 2O \text{ (or } O_2) + 4e^-$$

This reaction is easily promoted by forming the diffusion layer 8 which has good electron conductivity on the interface between the electrode 3 and the solid electolyte 1 as in the present invention. Hence, it is also possible to reduce the internal impedance of the cell.

A preferred example of the solid electrolyte to be used in the present invention is a $ZrO_2$ sintered body stabilized by 10 mol% of $Y_2O_3$ and preferred mixtures of the metals and their oxides to be used as the reference oxygen partial pressure source are, for example, Fe/FeO, Co/CoO, Cr/CrO, Ni/NiO and so forth.

The heat-treatment for activating the oxygen sensor is carried out preferrably at a temperature in the range of 1,000°–1,200° C. over a period of 5 to 60 hours in the air although heating can be for a period of up to 120 hours.

The present invention will be explained in further detail by the following examples. Samples Nos. A through M of the Comparative Examples and Examples are prepared respectively, as shown in Table 1. To each of the various metal powders of below 325 mesh (−325 mesh) is added 30% (weight ratio thereto) of $\alpha$-$Al_2O_3$ powder (−200 mesh) and dry-blended in a ball mill for about one hour to form a uniform mixture. After about 0.2 g of each mixture is packed into the solid electrolyte vessel, an oxygen sensor is produced in accordance with the above-described method. Each sample A–M is heated in an electric furnace under the conditions mentioned below to perform the diffusion treatment and the activation of the metal of the solid pole.

load characteristics with the progress of the diffusion treatment for the activation in comparison with Comparative Example 1, Sample K. In other words, it can be seen that the voltage drop of the sensor terminal becomes lower with the increase of the out-flow current from the sensor. However, Sample E, which is subjected to the diffusion treatment for the longest period (1,100° C.×108 hr.), exhibits considerable degradation of its characteristics. This is the degradation of characteristics arising from sintering of the Pt electrode itself or the grain growth of the Pt electrode due to the heat-treatment.

Figure 2:
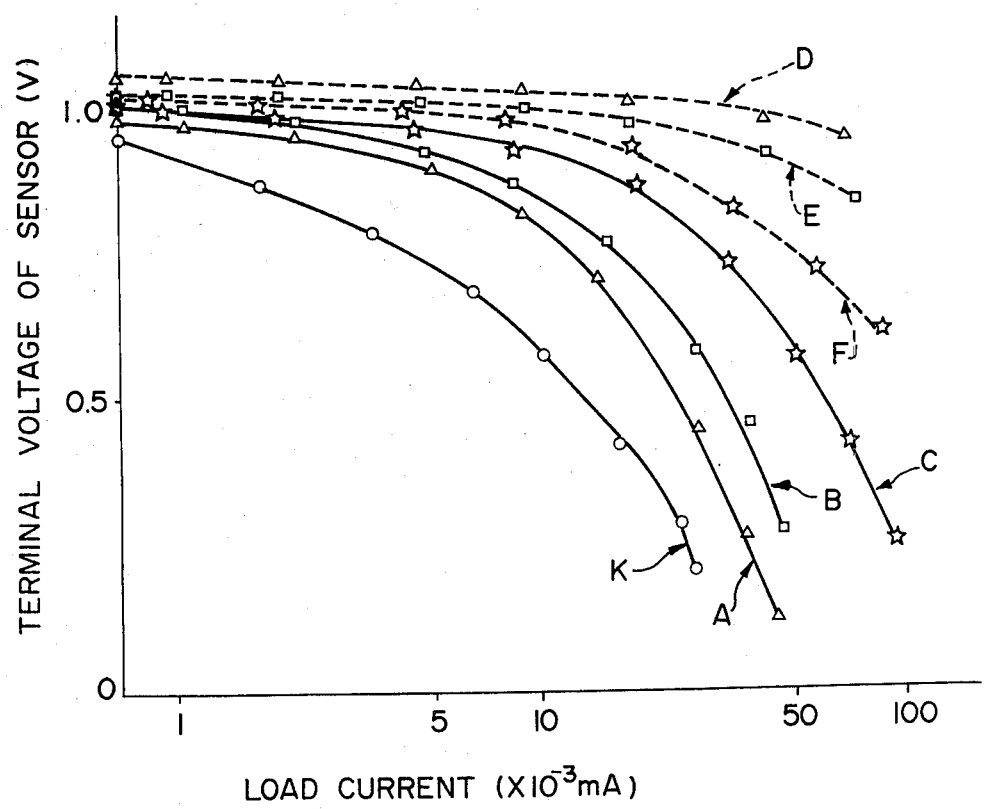
FIG. 2 is a diagram showing the load characteristics of the oxygen sensors obtained by Comparative Example 1 and Example 1.
Figure 3:
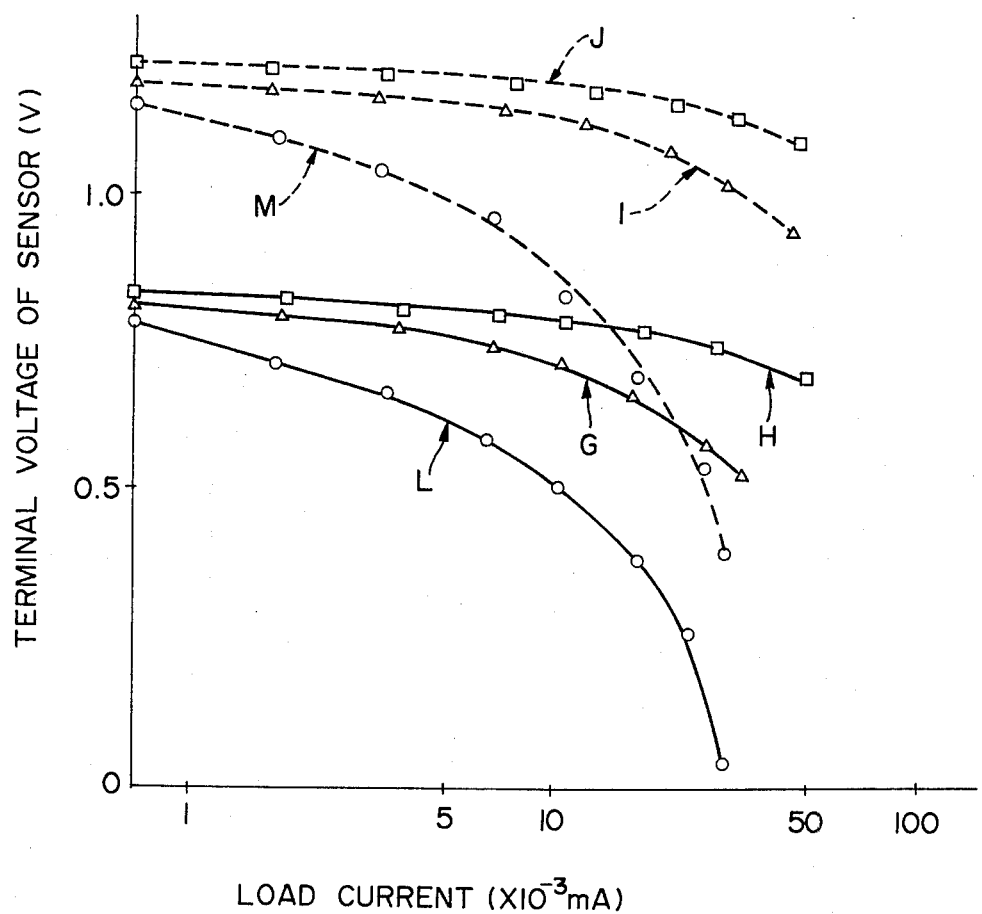
FIG. 3 is a diagram showing the load characteristics of the oxygen sensors obtained by Examples 2 and 3 and Comparative Examples 2 and 3.

FIG. 3 illustrates the load characteristics of the oxygen sensors of Examples 2, 3 and Comparative Examples 2 and 3 (Samples Nos. G, H, I, J and L, M, respectively) that use Ni or Cr powder as the metal for the solid pole. In the same way as in FIG. 2, it is obvious that in comparison with Comparative Examples 2 and 3 (Samples L and M), the oxygen sensors of the present invention (Samples G, H, I and J) exhibit the improvement in their load characteristics due to the diffusion treatment.

FIGS. 4 through 7 illustrate the sectional portion of the interface between the Pt electrode and the zirconia sintered body of the sample D, which is subject to the diffusion treatment in Example 1 at 1,100° C. for 60 hours, as observed by an EPMA under the following

TABLE 1

| Sample No. | Sample | Solid electrode | Diffusion treatment temp. (°C.) | time (hr) | Thickness of diffusion layer (mm) |
|---|---|---|---|---|---|
| A | Example 1 | Fe(−325 mesh) + 80%* $\alpha$-$Al_2O_3$ | 1000 | 1 | 0** |
| B | | " | 1100 | 12 | 0.05 |
| C | | " | " | 24 | 0.15 |
| D | | " | " | 60 | 0.40 |
| E | | " | " | 108 | 0.70 |
| F | | " | 1200 | 12 | 0.20 |
| G | Example 2 | Ni(−325 mesh) + 30% $\alpha$-$Al_2O_3$ | 1100 | 24 | 0.10 |
| H | | " | " | 60 | 0.35 |
| I | Example 3 | Cr(−325 mesh) + 30% $\alpha$-$Al_2O_3$ | 1100 | 24 | 0.15 |
| J | | " | " | 60 | 0.30 |
| K | Comp. Ex. 1 | Fe(−325 mesh) + 30% $\alpha$-$Al_2O_3$ | Only glass melting treatment (1000° C., 10 min) | | |
| L | Comp. Ex. 2 | Ni(−325 mesh) + 30% $\alpha$-$Al_2O_3$ | | | |
| M | Comp. Ex. 3 | Cr(−325 mesh) + 30% $\alpha$-$Al_2O_3$ | | | |

*% by weight.
**Interaction occurs only between Pt and Fe.
***Wall thickness of the solid electrolyte vessel used at 0.90 mm.

Example B shows a diffusion layer 0.05 mm thick, which is 5.6% of the 0.90 mm wall thickness of the solid electrolyte vessel, whereas Example E shows a diffusion layer 0.70 mm thick, which is on the order of 78% of the wall thickness of the vessel. However, a diffusion layer of a thickness as high as 85% of the wall thickness of the vessel can be provided, as previously indicated.

Evaluation of each sample in Table 1 is made in accordance with the following method. Each of the various oxygen sensors thus produced is uniformly heated at 500° C. in the electric furnace in the air and a load resistor ranging from 1 M Ohms to 10 K Ohms is sequentially wired between output leads of the sensor so as to increase step-wise the load current of the sensor. The terminal voltage (V) appearing between the output leads of the sensor is read out by a D.C. volt-meter of a 1000 M Ohms internal impedance. The results are shown in FIG. 2. As can be seen clearly, each oxygen sensor A–F of Example 1 exhibits the improvement in its analytical conditions;

| | |
|---|---|
| Accelerating voltage at the time of taking the picture of the secondary electron image | 25 kV |
| Sample current | 1–5 nA |
| Accelerating voltage at the time of taking the picture of characteristic X-ray image | 25 kV |
| Sample current | 0.05–0.1 $\mu$A |

Figure 4:
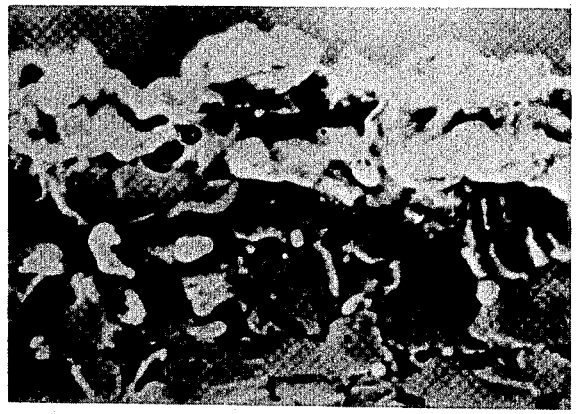
FIG. 4 is a photograph of the section of the interface of the platinum electrode and the zirconia sintered body of the oxygen sensor of Sample D, Example 1 as observed by an Electoron Probe Micro Analyzer (EPMA)

In the photograph of FIG. 4, it shows a porous platinum electrode is formed on the zirconia sintered body having zirconia particles of 10–15 microns.

Figure 5:
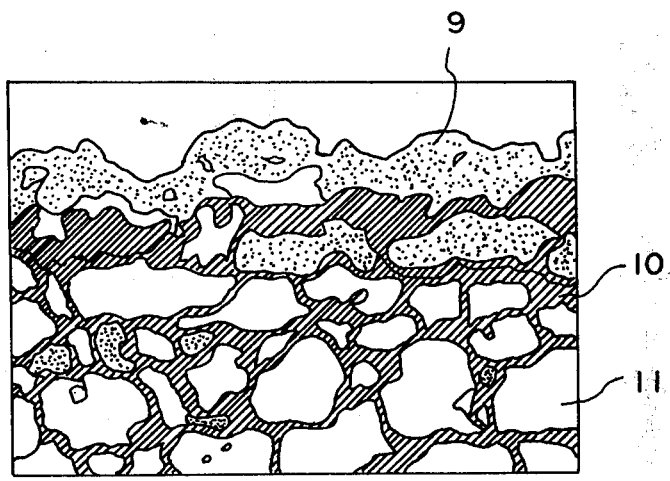
FIG. 5 is a schematic view corresponding to the photograph of FIG. 4.

FIG. 5 is a schematic view corresponding to the photograph of FIG. 4 wherein 9 represents the Pt electrode portions, 10 the Fe portion diffused in the grains and 11 the $ZrO_2$ grains.

Figure 6:
FIG. 6 is a photograph of the above-mentioned sectional portion as observed by characteristic X-rays of Pt (L$\alpha$ rays); and, FIG. 7 is a photograph of the above-mentioned sectional portion as observed by characteristic X-rays of Fe (K$\alpha$ rays).

FIG. 6 is a characteristic X-ray image (Lα rays) of Pt and it is observed that the electrode is attached in the thickness of 10-25 microns.

Figure 7:
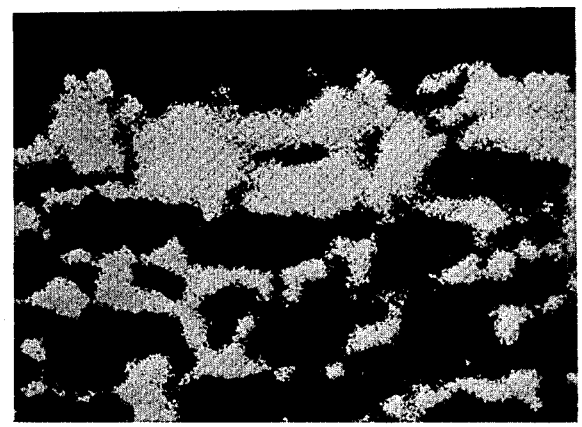

FIG. 7 is a characteristic X-ray image (Kχ rays) of Fe and it is observed that Fe is diffused markedly in the Pt electrode portions and the grains of the zirconia sintered body.

As can be appreciated clearly from the foregoing description, the oxygen sensor subjected to the activation treatment in accordance with the present invention has excellent performance, such as its good low temperature performance. The method of the present invention can be adapted not only specifically to the oxygen sensor for cars but also to an oxygen-meter for measuring the oxygen concentration in a molten metal at the time of metal refining, and can also be employed as an effective means for lowering the internal resistance of a solid cell.

What is claimed is:

1. A method of activating and using an oxygen concentration cell having metal electrodes formed on both the inner and outer wall surfaces of a solid electrolyte vessel and a solid pole as a reference oxygen partial pressure source consisting of a metal alone or a mixture of said metal and its oxide packed into said vessel, comprising activating said oxygen concentration cell by heat-treating said oxygen concentration cell in the presence of air to diffuse said metal of the reference oxygen partial pressure source into the solid electrolyte through said inner wall surface metal electrode, said heat treatment comprising heating at a temperature in the range of 1,000°-1,200° C. over a period of 5-120 hours in the air, and then using the cell to measure oxygen concentration at temperatures below 1,000° C.

2. The activation method of claim 1 wherein the heat-treatment of the oxygen concentration cell is carried out in such a manner that the diffusion layer is from about 5% to 85% of the wall thickness of said solid electrolyte vessel.

3. The activation method of claim 1 wherein a mixture of the metal and its oxide packed as said solid pole is selected from the group consisting of Fe/FeO, Co/CoO, Cr/CrO and Ni/NiO.

4. The activation method of claim 1 wherein a sintering-inhibiting agent is admixed in said solid pole.

5. The activation method of claim 4 wherein said sintering-inhibiting agent is an alumina powder.

* * * * *